US00PP35888P2

(12) United States Plant Patent
Tashiro

(10) Patent No.: US PP35,888 P2
(45) Date of Patent: Jun. 25, 2024

(54) ***LOBELIA* PLANT NAMED 'Balspringlav'**

(50) Latin Name: *Lobelia erinus*
Varietal Denomination: Balspringlav

(71) Applicant: Ball Horticultural Company, West Chicago, IL (US)

(72) Inventor: Rebecca M. Tashiro, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/123,805

(22) Filed: Mar. 20, 2023

(51) Int. Cl.
*A01H 5/02* (2018.01)
*A01H 6/26* (2018.01)

(52) U.S. Cl.
USPC ..... Plt./451
CPC ..... *A01H 6/268* (2018.05)

(58) Field of Classification Search
USPC ..... Plt./451
CPC ..... A01H 5/02
See application file for complete search history.

(56) References Cited

PUBLICATIONS https://www.guiniridge.com/wp-content/uploads/2022/11/2024-Ball-Flora-Plant-Introductions-Lynne-Blye.pdf; Nov. 2022; 2 pages.*
https://www.ballseed.com/PlantInfo/?phid=039307444002843; Jan. 7, 2024; 2 pages.*

* cited by examiner

*Primary Examiner* — Kent L Bell
(74) *Attorney, Agent, or Firm* — Audrey Charles

(57) ABSTRACT

A new and distinct cultivar of *Lobelia* plant named 'Balspringlav', characterized by its light lavender-colored flowers having a white eye with reddish-purple markings, medium green-colored foliage, and moderately vigorous, compact, upright-mounded, is disclosed.

1 Drawing Sheet

Latin name of genus and species of plant claimed: *Lobelia erinus*.

Variety denomination: 'Balspringlav'.

BACKGROUND OF THE INVENTION

The present invention relates to a new and distinct cultivar of *Lobelia* plant botanically known as *Lobelia erinus* and hereinafter referred to by the cultivar name 'Balspringlav'.

The new cultivar originated in a controlled breeding program in Guadalupe, California during September 2018. The objective of the breeding program was the development of heat tolerant *Lobelia* cultivars having a long flowering season with a compact, upright-mounded growth habit.

The new *Lobelia* cultivar is the result of cross-pollination. The female (seed) parent of the new cultivar is the proprietary *Lobelia erinus* breeding selection coded LOB-00336-001, not patented, characterized by its dark lavender-colored flowers having a white eye, medium green-colored foliage, low growth vigor and compact-mounded growth habit. The male (pollen) parent of the new cultivar is the proprietary *Lobelia erinus* breeding selection coded LOB-00345-001, not patented, characterized by its light lavender-colored flowers, medium green-colored foliage, and moderately vigorous, mounded growth habit. The new cultivar was selected as a single flowering plant within the progeny of the above stated cross-pollination during April 2019 in a controlled environment in Guadalupe, California.

Asexual reproduction of the new cultivar by terminal stem cuttings since April 2019 in Guadalupe, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balspringlav' as a new and distinct cultivar of *Lobelia* plant:

1. Light lavender-colored flowers having a white eye with reddish-purple markings;
2. Medium green-colored foliage; and
3. Moderately vigorous, compact, upright-mounded growth habit.

Plants of the new cultivar differ from plants of the female parent primarily in having lighter lavender-colored flowers, more branches per plant, and increased growth vigor. Plants of the new cultivar differ from plants of the male parent primarily in having flowers with a white eye with reddish-purple markings, more branches per plant, and a more compact growth habit.

Of the many commercially available *Lobelia* cultivars, the most similar in comparison to the new cultivar is Early Springs Dark Blue 'KLELE12472', U.S. Plant Pat. No. 25,289. However, in comparison, plants of the new cultivar differ from plants of 'KLELE12472' in at least the following characteristics:

1. Plants of the new cultivar have lighter lavender-colored flowers than plants of 'KLELE12472'; and
2. Plants of the new cultivar have a larger corolla diameter than plants of 'KLELE12472'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balspringlav'. The plants were approximately 13-weeks old. The plants were grown in 4.5-inch containers for approximately 9 weeks in a greenhouse in West Chicago, Illinois. Plants were given two pinches, one at transplant and one three weeks after transplant.

DETAILED BOTANICAL DESCRIPTION

Figure 1:
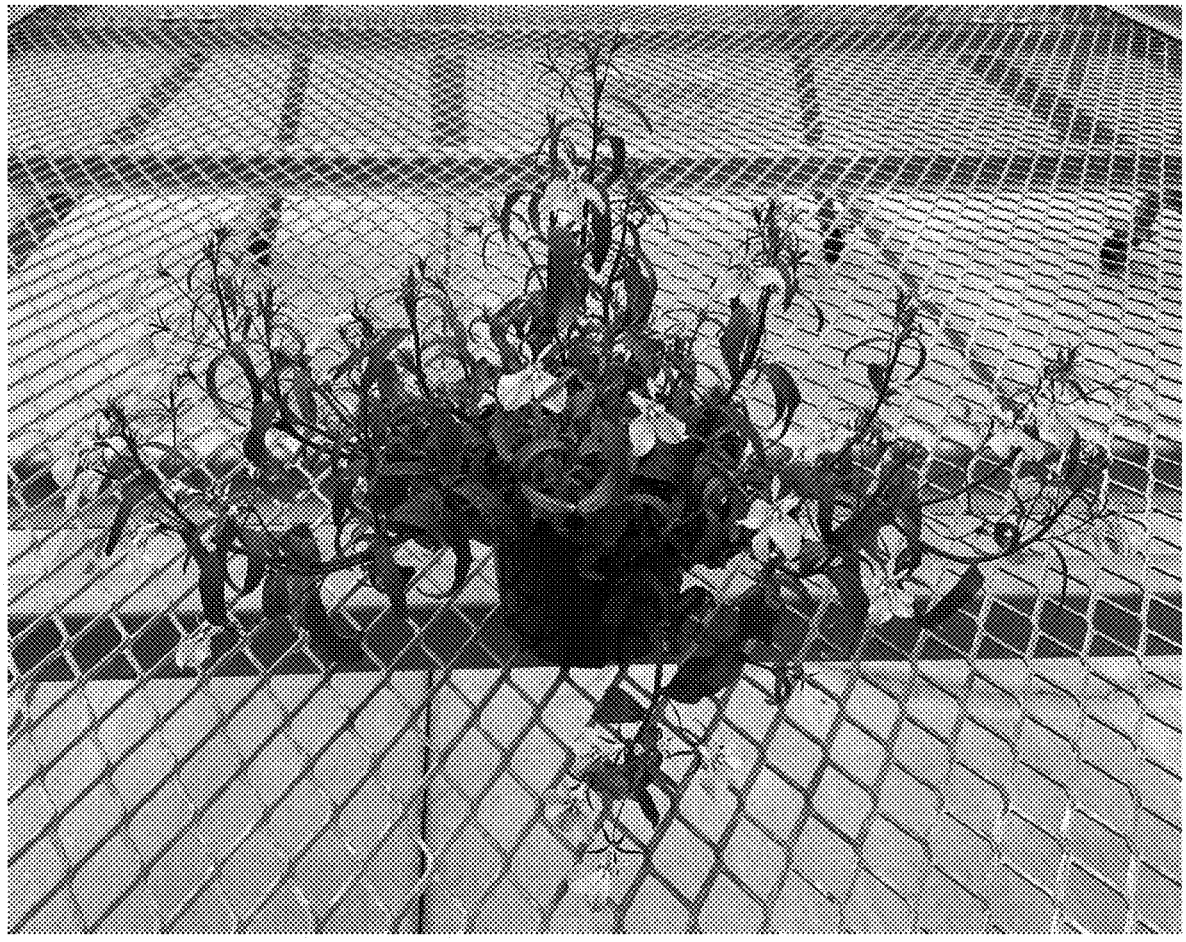
FIG. 1 illustrates a side view of the overall growth and flowering habit of 'Balspringlav'.
Figure 2:
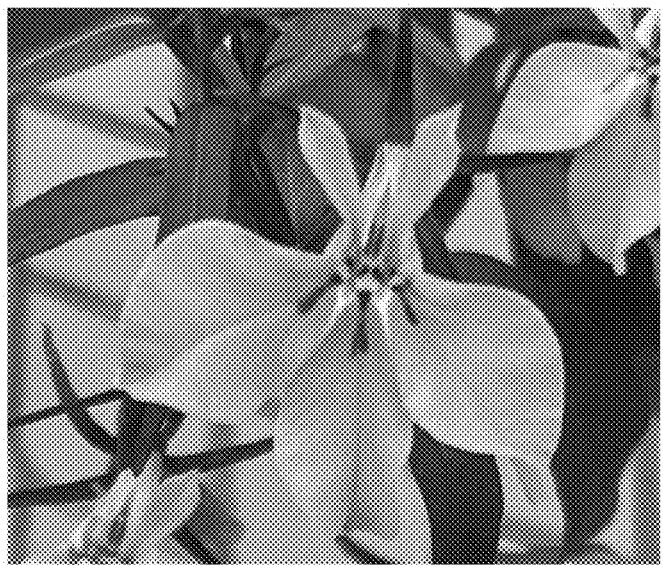
FIG. 2 illustrates a close-up view of a flower of 'Balspringlav'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in January 2023 under natural light conditions in Naperville, Illinois.

The following descriptions and measurements describe approximately 13-week-old plants produced from cuttings from stock plants and grown in a polycarbonate greenhouse under conditions comparable to those used in commercial practice. The plants were grown in West Chicago, Illinois in 4.5-inch containers for approximately 9 weeks utilizing a soilless growth medium. Plants were given two pinches, one at transplant and one three weeks after transplant. Greenhouse temperatures were maintained at approximately 68° F. to 70° F. (20° C. to 21° C.) during the day and approximately 60° F. to 65° F. (16° C. to 18° C.) during the night. Supplemental lighting was used. Measurements and numerical values represent averages of typical plants.

Botanical classification: *Lobelia erinus* 'Balspringlav'.

Parentage:

*Female parent*.—Proprietary *Lobelia erinus* breeding selection coded LOB-00336-001, not patented.

*Male parent*.—Proprietary *Lobelia erinus* breeding selection coded LOB-00345-001, not patented.

Propagation:

*Type cutting*.—Terminal stem.

*Time to initiate roots*.—Approximately 6 to 9 days.

*Time to produce a rooted cutting*.—Approximately 24 to 28 days.

*Root description*.—Fine to medium, fibrous.

*Rooting habit*.—Freely branching.

Plant description:

*Commercial crop time*.—Approximately 7 to 9 weeks from a rooted cutting to finish in a 10 cm container.

*Growth habit and general appearance*.—Moderately vigorous, compact, upright-mounded growth habit.

*Size*.—Height from soil level to top of plant plane: Approximately 17.5 cm. Width: Approximately 38.0 cm.

*Branching habit*.—Freely branching, pinching enhances lateral branching. Quantity of branches per plant: Approximately 8 main branches with approximately 4 lateral branches per main branch.

*Lateral branch*.—Shape: Square in cross section. Strength: Strong, flexible. Length: Approximately 21.0 cm. Diameter: Approximately 2.0 mm to 3.0 mm. Length of central internode: Approximately 2.1 cm. Texture: Glabrous. Color of young stems: 146A. Color of mature stems: 137A.

Foliage description:

*General description*.—Quantity of leaves per branch: Approximately 9. Fragrance: None detected. Form: Simple. Arrangement: Alternate.

*Leaves*.—Aspect: Acute angle to stem tip downward turning. Shape: Narrowly elliptic. Margin: Shallowly serrate, sparsely ciliate. Apex: Acute. Base: Sessile. Venation pattern: Pinnate. Length of mature leaf: Approximately 5.5 cm. Width of mature leaf: Approximately 1.3 cm. Texture of upper and lower surfaces: Glabrous. Color of upper surface of young and mature foliage: 137A with venation of 137B. Color of lower surface of young and mature foliage: Closest to 138B with venation of 138A.

Flowering description:

*Flowering habit*.—'Balspringlav' is freely flowering under outdoor conditions with substantially continuous blooming from early spring through summer and year-round in a greenhouse environment.

Inflorescence description:

*General description*.—Type: Loose raceme. Quantity per plant: Approximately 9. Fragrance: None detected. Length or height of inflorescence: Approximately 7.0 cm to 8.5 cm. Width of inflorescence: Approximately 6.0 cm to 8.0 cm. Quantity of fully-open flowers per inflorescence: Approximately 3 to 5.

Flower description:

*Type*.—Single, zygomorphic, bilabiate.

*Bud just before opening*.—Shape: Obovoid. Length: Approximately 1.0 cm. Diameter at distal end: Approximately 4.0 mm. Diameter at proximal end: Approximately 2.0 mm. Texture: Glabrous. Color: 145B.

*Corolla*.—Shape: Bilabiate having an upper lip of two narrow lobes and a lower lip of three lobes. Lobes are fused at the base forming a tube that is split between the two upper lobes. Aspect: Facing upward and outward. Width: Approximately 1.9 cm. Length: Approximately 2.2 cm. Depth: Approximately 1.7 cm.

*Upper lobes*.—Shape: Oblanceolate. Margin: Entire, ciliate. Apex: Mucronate. Length from throat: Approximately 9.0 mm. Width: Approximately 3.0 mm. Texture of upper (inner) surface: Sparsely pubescent near base. Texture of lower (outer) surface: Glabrous. Color of upper (inner) surface when first open: Between 91A and 91B. Color of lower (outer) surface when first open: Between 91A and 91B. Color of upper (inner) surface when fully open: 91B. Color of lower (outer) surface when fully open: Between 91B and 91C.

*Lower lobes*.—Shape: Obovate. Margin: Entire, ciliate at base. Apex: Mucronate. Length from throat: Approximately 1.3 cm. Width: Approximately 9.0 mm. Texture of upper (inner) surface: Sparsely pubescent near base. Texture of lower (outer) surface: Glabrous. Color of upper (inner) surface when first open: Between 91A and 91B with basal margins of NN155D and a basal central stripe and tint of N78A. Color of lower (outer) surface when first open: Between 91B and 91C. Color of upper (inner) surface when fully open: 91B with basal margins of NN155D and a basal central stripe of N78A. Color of lower (outer) surface when fully open: Between 91C and 91D.

*Corolla tube*.—Length: Approximately 8.0 mm. Width at opening: Approximately 4.0 mm. Width at base: 2.0 mm. Texture of inner surface: Glabrous with sparse pubescence at throat opening. Texture of outer surface: Glabrous. Color of inner surface: NN155D with a zigzag stripe of N78A near throat opening and two nectary tracks of 144A. Color of outer surface: Between 91C and 91D with 144C opposite the two nectary tracks.

*Calyx*.—Shape: Star. Length: Approximately 1.2 cm. Diameter: Approximately 2.0 cm.

*Sepals*.—Quantity per flower: 5. Shape: Lanceolate. Margin: Entire. Apex: Acute. Base: Fused into cup-like structure. Length of free portion: Approximately 1.0 cm. Width: Approximately 1.0 mm. Texture of inner and outer surface: Glabrous. Color of inner and outer surfaces: 137A.

*Pedicel*.—Strength: Strong, flexible. Aspect: At an acute angle. Length: Approximately 3.0 cm. Diameter: Approximately 1.0 mm. Texture: Glabrous. Color: 137A.

*Reproductive organs*.—Androecium: Stamen quantity: 5 per flower, upper half of filaments connate. Stamen length: Approximately 1.3 cm. Filament color: NN155D with a faint overlay of N87A near anther. Anther shape: Oblong. Anther length: Approximately 2.0 mm. Anther color: N92C. Pollen amount: Abundant. Pollen color: NN155D. Gynoecium: Pistil quantity: 1 per flower. Pistil length: Approximately 9.0 mm. Stigma shape: Bilobate. Stigma length: Approximately 1.0 mm. Stigma color: 86A. Style length: Approximately 6.0 mm. Style color: 144A. Ovary length: Approximately 2.0 mm. Ovary color: 137A.

Seed and fruit production: Neither seed nor fruit production has been observed.

Disease and pest resistance: Resistance to pathogens and pests common to *Lobelia* has not been observed.

What is claimed is:

1. A new and distinct cultivar of *Lobelia* plant named 'Balspringlav', substantially as herein illustrated and described.

* * * * *